United States Patent [19]

Klein

[11] Patent Number: 5,435,297
[45] Date of Patent: Jul. 25, 1995

[54] MEDICAL DEVICE FOR INHALING METERED AEROSOLS

[75] Inventor: Christoph Klein, Bahnhofstrasse 102, D-53757 St. Augustin, Germany

[73] Assignees: Christoph Klein, St. Augustin; Peter-Christian Sroka, Mülheim/Ruhr, both of Germany; a part interest

[21] Appl. No.: 167,850
[22] PCT Filed: Aug. 28, 1992
[86] PCT No.: PCT/DE92/00723
    § 371 Date: Jun. 29, 1994
    § 102(e) Date: Jun. 29, 1994
[87] PCT Pub. No.: WO93/04718
    PCT Pub. Date: Mar. 18, 1993

[30] Foreign Application Priority Data

Aug. 29, 1991 [DE] Germany .......... 41 28 666.9
Oct. 28, 1991 [DE] Germany .......... 9113361 U
Feb. 20, 1992 [DE] Germany .......... 9202198 U
Apr. 9, 1992 [DE] Germany .......... 9204938 U

[51] Int. Cl.⁶ ................................ A61M 11/00
[52] U.S. Cl. .................. 128/200.23; 222/402.13; 239/296
[58] Field of Search .......... 128/200.14, 200.18, 128/200.23, 203.12, 203.15; 222/402.13, 182; 239/296, 310, 315, 422

[56] References Cited

U.S. PATENT DOCUMENTS

| | | | |
|---|---|---|---|
| 3,302,834 | 8/1965 | Alsep | 128/200.23 |
| 3,320,952 | 5/1967 | Wright | 128/200.23 |
| 3,848,807 | 11/1974 | Pastida | 239/296 |
| 3,980,074 | 9/1976 | Watt et al. | |
| 3,994,421 | 11/1976 | Hansen | 222/402.13 |

FOREIGN PATENT DOCUMENTS

| | | | |
|---|---|---|---|
| 0009667 | 4/1980 | European Pat. Off. | |
| 0308524 | 3/1989 | European Pat. Off. | |
| 1378213 | 10/1964 | France | |
| 9113361 | 1/1992 | Germany | |
| 9202198 | 7/1992 | Germany | |
| 6509710 | 1/1966 | Netherlands | 128/200.23 |
| 2074454 | 11/1981 | United Kingdom | 128/200.23 |

Primary Examiner—Edgar S. Burr
Assistant Examiner—Virendra Srivastava
Attorney, Agent, or Firm—Robert W. Becker & Associates

[57] ABSTRACT

A medical device for inhaling metered aerosol has a cylindrical housing with a receiving chamber for receiving an aerosol container and first main air channels extending axially within the housing. A mouthpiece is coaxially connected to the housing. An atomizing and vortexing chamber is delimited by the housing and the mouthpiece. Second main air channels extend within the mouthpiece and communicate with the first main air channels. A partition is positioned between the receiving chamber and the atomizing and vortexing chamber. The partition has a stepped bore with a first section and a second section, the first section having a larger diameter than the second section. The first section opens into the receiving chamber and the second section opens into the atomizing and vortexing chamber to form an aerosol outlet. Branch air channels extend at a slant to an axial direction of the medical device within the partition so as to surround the stepped bore. The branch air channels are connected to the first main air channels and open into the atomizing and vortexing chamber.

15 Claims, 2 Drawing Sheets

MEDICAL DEVICE FOR INHALING METERED AEROSOLS

BACKGROUND OF THE INVENTION

The invention relates to a medical device for aerosol containers, in which the release of the aerosol and inhalation take place simultaneously or by switching to an intermediate chamber, into which the medicament is first sprayed and then inhaled from that chamber. Conventional aerosol containers frequently have a nozzle needle which can be pushed into the aerosol container in order to spray out the medicament atomized to the fullest possible extent for inhalation.

An inhalation device in accordance with EP 00 08 667 A1 has a housing with a receiving chamber to hold the aerosol container, to which chamber are coaxially connected a vortexing chamber and a mouthpiece. A support, which has a central stepped bore, projects relatively deeply into the vortexing chamber. Into the section of the stepped bore having the larger bore diameter the nozzle needle of the aerosol container introduced into the receiving chamber can be inserted.

Air inlets, through which the air breathed during inhaling is sucked into the vortexing chamber in order to convey the medicament in the vortexing chamber through the mouthpiece into the lungs, open into the vortexing chamber at a relatively large distance from the stepped bore. Located in the mouthpiece area are separate inlet and outlet valves which make it possible, on the one hand, to inhale through the vortexing chamber, and, on the other hand, to exhale independently of the vortexing chamber. The air inlets opening into the vortexing chamber are of relatively small dimensions, and unsuitable, due to their spatial position, to exert a significant effect on the atomization and vortexing of the medicament. The device is relatively long, corresponding to roughly three times the height of a conventional aerosol container, so that it is impossible in general to carry the device around all the time as a hand or pocket device.

With an inhaler in accordance with U.S. Pat. No. 4,852,561, the mouthpiece and the housing forming the aerosol container receiving chamber are located coaxially one behind the other, whereby the opening mechanism for the aerosol container metering valve is fitted to the end of the inhaler opposite the mouthpiece. The receiving chamber for the aerosol container forms a medicament vortexing chamber, into which the relatively small sized air inlets open. When opening the aerosol container metering valve, the medicament released with the propellant agent is deflected about an angle of approximately 90°, so that the metering valve can become clogged early.

In using conventional inhalers, there is a danger, due to the relatively small air inlets opening into the vortexing chamber, of so-called "anxiety over breathing", which is additionally reinforced if valve components are located upstream of the inhalation mouthpiece that impair free respiration and form an additional obstruction on which the medicament can collect.

The object of the invention is to create a medical appliance for inhaling metered aerosols in such a way that with the device the atomization and vortexing of the medicament leaving the aerosol container by way of the air inhaled through the device is improved in comparison with conventional devices in order to achieve that the highest possible quantity of medicament is introduced into the bronchial area, and the frequently occurring anxiety over breathing is largely eliminated.

SUMMARY OF THE INVENTION

The medical device for inhaling metered aerosol according to the present invention is primarily characterized by:

a cylindrical housing with a receiving chamber for receiving an aerosol container;

first main air channels extending axially within the housing;

a mouthpiece coaxially connected to the housing;

an atomizing and vortexing chamber delimited by the housing and the mouthpiece;

second main air channels extending within the mouthpiece and communicating with the first main air channels;

a partition positioned between the receiving chamber and the atomizing and vortexing chamber, the partition having a stepped bore with a first section and a second section, the first section having a larger diameter than the second section, wherein the first section opens into the receiving chamber and the second section opens into the atomizing and vortexing chamber to form an aerosol outlet; and branch air channels extending at a slant to an axial direction of the medical device within the partition so as to surround the stepped bore, the branch air channels connected to the first main air channels and opening into the atomizing and vortexing chamber.

Preferably, the housing has a plurality of the first main air channels. Each first main air channel has a lateral connecting line and opens at an end face of the housing facing the mouthpiece.

Advantageously, the first main air channels connect the receiving chamber with the atomizing and vortexing chamber.

The partition comprises connecting channels for connecting the first main air channels to the atomizing and vortexing chamber, wherein the connecting channels are arranged to surround the branch air channels and open into the atomizing and vortexing chamber such that air flowing through the connecting channels generates a substantially axially directed mantle flow along an inner wall surface of the atomizing and vortexing chamber.

The mouthpiece has a cylindrical section open at an end proximal to a user, wherein an inner diameter of the cylindrical section corresponds substantially to an inner diameter of a portion of the atomizing and vortexing chamber defined by the mouthpiece.

The housing has preferably an inner wall surface with axially extending spacer stays. The housing and the mouthpiece expediently have corresponding threads for threading the housing and the mouthpiece together.

In a preferred embodiment, the aerosol outlet has a shape that conically widens toward the atomizing and vortexing chamber, wherein an opening angle of the aerosol outlet is between 60° and 120°, preferably substantially 90°.

The branch air channels advantageously open into the conically widening shape of the aerosol outlet.

The branch air channels and the connecting channels open radially into the atomizing and vortexing chamber.

The mouthpiece has a diameter of 12-18 mm and has a direct transition into a mouthpiece opening, preferably, the diameter is substantially 15 mm.

Advantageously, the housing and the mouthpiece are threaded together to attain predetermined rotational positions for controlling an amount of air flow through the second main air channels, the branch air channels, and the connecting channels.

Expediently, the first main air channels extend over an entire length of the housing.

Anxiety over breathing is overcome by providing correspondingly large dimensioned main air channels resulting in an adequate air supply.

Optimum inhalation of a large quantity of medicament is ensured by means of an intermediate path via an atomizing and vortexing chamber, into which part of the air is fed through the secondary branch channels, preferably into the immediate vicinity of the stepped bore and thus the aerosol container metering valve, whereby an additional atomization of the medicament down to a size of 3 μm and smaller, the so-called lung and bronchial-suitable fraction, occurs.

DESCRIPTION OF PREFERRED EMBODIMENTS

Figure 1:
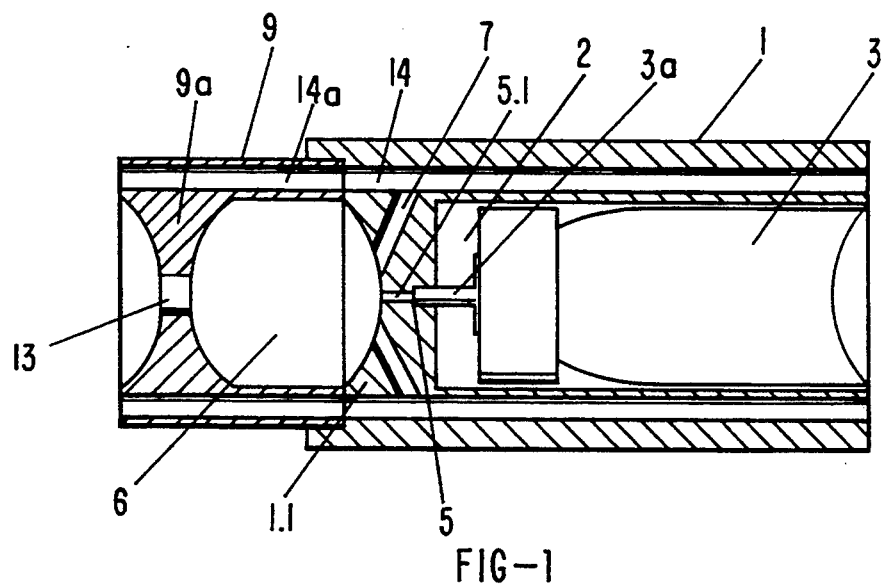
FIGS. 1-5 illustrate various embodiments of the inventive inhalation device.

The device illustrated in FIG. 1 comprises a housing, to which a mouthpiece 9 can be axially connected, with a receiving chamber 2 which is limited on one side by a partition 1.1 that has a stepped bore 5. The chamber 2 accommodates an aerosol container 3, the nozzle needle 3a of which is inserted into the larger diameter section of the stepped bore 5. The receiving chamber 2 is surrounded by axially orientated first main air channels 14 which have a large orifice cross section. Connected to the smaller diameter section 5.1 of the stepped bore 5 is a vortexing chamber 6, into which the branch air channels, connected with the main air channels 14 and extending through the partition 1.1 open preferably near the nozzle opening.

The mouthpiece 9 has a cylindrical section forming part of the vortexing chamber 6. In the area of the mouthpiece 9, the vortexing chamber 6 is limited by a wall 9a with a central opening 13 and is provided with second main air channels 14a connected to the main air channels 14.

The housing 1 and the mouthpiece 9 are embodied with a double wall for forming the main air channels 14 and 14a, with stays extending between the cylinder walls.

The mouthpiece 9 can be connected to the housing 1 by means of, for example, a thread. At its outer end, the mouthpiece 9 can assume a shape suitable for the mouth, e.g. an oval shape.

The walls of the vortexing chamber 6 are preferably polished. The branch air channels 7 are inclined, and the stepped bore 5, 5.1 so arranged that the aerosol leaving the container 3 is optimally atomized and vortexed.

Figure 2:
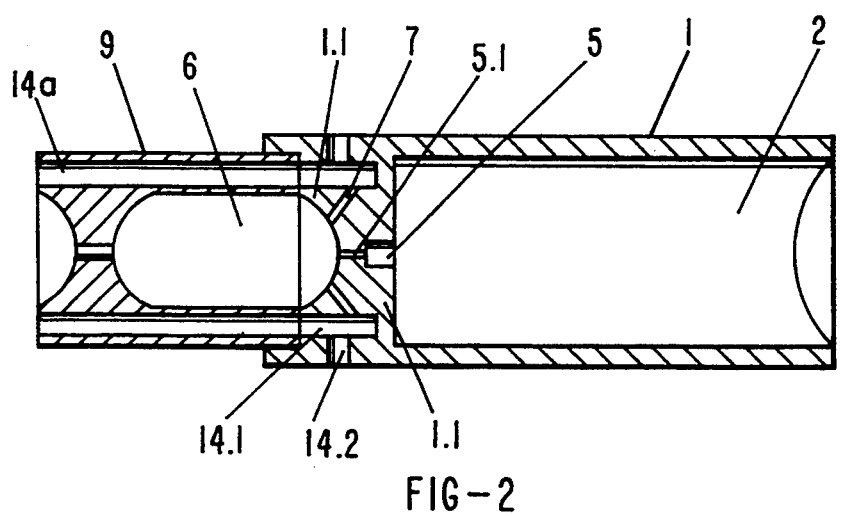

With the version according to FIG. 2 (see DE-GM 9113831.0 published on Jan. 30, 1992 upon which the partial priority of Oct. 28, 1991 is based), open, relatively short, axially orientated main air channels 14.1, into which lateral connecting channels 14.2 extending from the outer mantle surface of the housing 1 open, are provided on the side of the housing 1 facing the mouthpiece 9. The branch air channels 7 are connected to channels 14.1, and open into the vortexing chamber 6.

Figure 3:
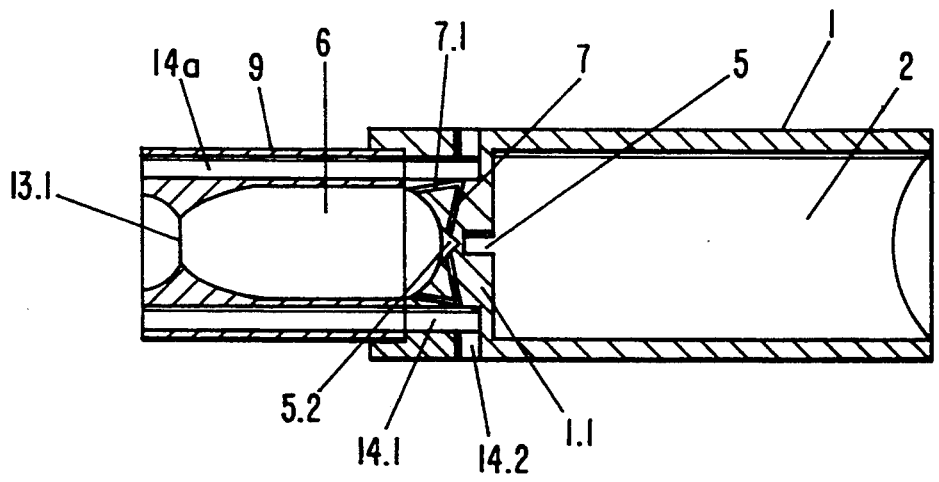

According to FIG. 3 (see DE-GM 9202198.0 of Feb. 20, 1992, published on Jul. 23, 1992, upon which the partial priority of Feb. 20, 1992 is based), the stepped bore section with the smaller diameter is widened into a nozzle-shaped or conical aerosol outlet 5.2 opening into the vortexing chamber 6. The orifice angle of the outlet 5.2 is between 60° and 120°, preferably approximately 90°, whereby the branch air channels 7 open into this outlet 5.2.

Additional branch air channels 7.1, which also branch off from the main air channels 14.1, are oriented in the vortexing chamber 6 in such a way that a mantle flow along the walls of the vortexing chamber 6 is generated.

The central opening 13.1, connecting with the vortexing chamber 6, is of a relatively large cross section.

Figure 4:
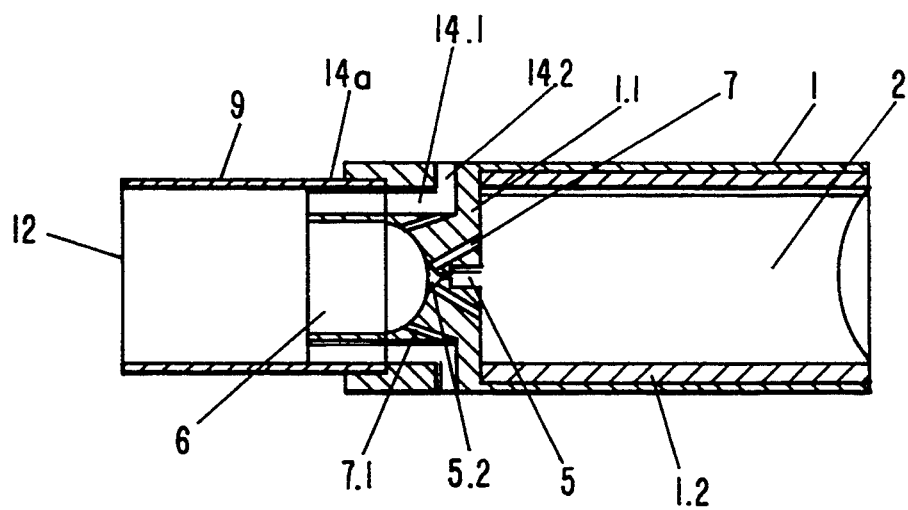

According to FIG. 4 (see unpublished DE-GM 9204838.9 upon which the partial priority of 9 Apr. 1992 is based), the housing 1 is provided, in contrast to FIG. 3, with axially oriented spacing stays 1.2 on the inner wall, so that axially oriented air channels remain open between the aerosol container and the inner wall after the insertion of an aerosol container into the receiving chamber 2. Branch air channels 7 connecting with the receiving chamber 2 open into the aerosol outlet 5.2, which widens into the shape of a nozzle.

The mouthpiece 9 consists of a cylindrical tube, the interior of which forms part of the vortexing chamber 6. The interior has a uniform cylindrical cross-section essentially over its entire length, so that the mouthpiece orifice 12 has the same cross-section as the interior of the mouthpiece 9 positioned upstream.

The main air channels 14.1 and the connecting channels 14.2 as well as the branch air channels 7.1 opening into the vortexing chamber 6 are essentially equivalent to the embodiment of FIG. 3. In the embodiment in accordance with FIG. 4, the interior of the mouthpiece 9 has a diameter of 12-18 mm, preferably 15 mm, whereby the main air channels 14a are relatively short so that the air exiting therefrom forms a mantle flow along the inner mouthpiece wall.

Figure 5:
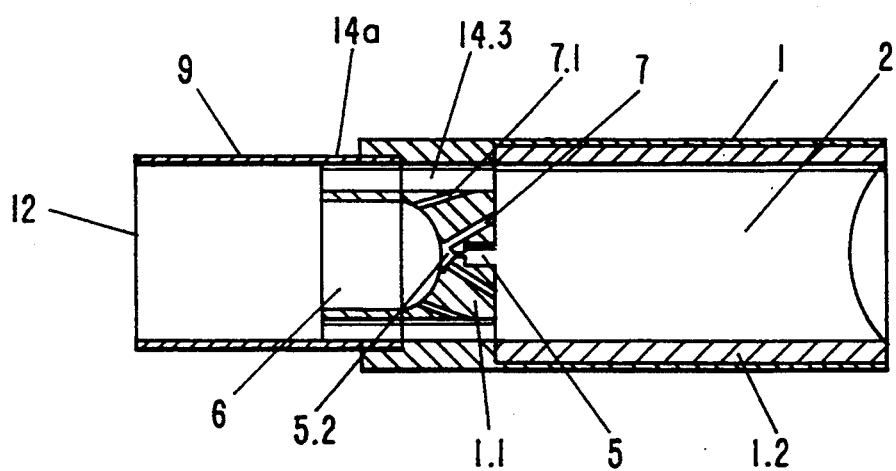

In the version according to FIG. 5 (without priority), axially oriented main air channels 14.3, extending through the housing 1 provided with spacing webs 1.2, are directly connected to the receiving chamber 2 (in contrast to FIG. 4) so that, for example, the laterally outgoing connecting channels 14.2 of FIG. 4 are dispensed with.

The housing 1 and the mouthpieces 9 preferably consist of V2A or V4A steel, aluminum or plastic.

The linear arrangement of the device particularly facilitates and optimizes use in the recumbent position, e.g. at night or with bedridden patients.

The mouthpieces 9 can be screwed to the housing 1 in various fixed rotational positions for controlling the quantity of air flowing through the second main air channels 14a on the one hand, and through the branch air channels 7; 7.1 on the other hand.

The present invention is, of course, in no way restricted to the specific disclosure of the specification and drawings, but also encompasses any modifications within the scope of the appended claims.

What is claimed is:

1. A medical device for inhaling metered aerosol, comprising:

a cylindrical housing with a receiving chamber for receiving an aerosol container;

first main air channels extending axially within said housing;

a mouthpiece coaxially connected to said housing;

an atomizing and vortexing chamber delimited by said housing and said mouthpiece;

second main air channels extending within said mouthpiece and communicating with said first main air channels;

a partition positioned between said receiving chamber and said atomizing and vortexing chamber, said partition having a stepped bore with a first section and a second section, said first section having a larger diameter than said second section, wherein said first section opens into said receiving chamber and said second section opens into said atomizing and vortexing chamber to form an aerosol outlet;

branch air channels extending at a slant to an axial direction of said medical device within said partition so as to surround said stepped bore, said branch air channels connected to said first main air channels and opening into said atomizing and vortexing chamber.

2. A medical device according to claim 1, wherein:

said housing has a plurality of said first main air channels;

each said first main air channel has a lateral connecting line; and each said first main air channel opens at an end face of said housing facing said mouthpiece.

3. A medical device according to claim 1, wherein said first main air channels connect said receiving chamber with said atomizing and vortexing chamber.

4. A medical device according to claim 1, wherein said partition comprises connecting channels for connecting said first main air channels to said atomizing and vortexing chamber, said connecting channels arranged to surround said branch air channels and opening into said atomizing and vortexing chamber such that air flowing through said connecting channels generates a substantially axially directed mantle flow along an inner wall surface of said atomizing and vortexing chamber.

5. A medical device according to claim 1, wherein said mouthpiece has a cylindrical section open at an end proximal to a user, wherein an inner diameter of said cylindrical section corresponds substantially to an inner diameter of a portion of said atomizing and vortexing chamber defined by said mouthpiece.

6. A medical device according to claim 1, wherein said housing has an inner wall surface with axially extending spaces stays.

7. A medical device according to claim 1, wherein said housing and said mouthpiece have corresponding threads for threading said housing and said mouthpiece together.

8. A medical device according to claim 1, wherein said aerosol outlet has a shape that conically widens toward said atomizing and vortexing chamber, wherein an opening angle of said aerosol outlet is between 60° and 120°.

9. A medical device according to claim 8, wherein said opening angle is substantially 90°.

10. A medical device according to claim 8, wherein said branch air channels open into said conically widening shape of said aerosol outlet.

11. A medical device according to claim 3, wherein said branch air channels and said connecting channels open radially into said atomizing and vortexing chamber.

12. A medical device according to claim 1, wherein said mouthpiece has a diameter of 12–18 mm and has a direct transition into a mouthpiece opening.

13. A medical device according to claim 12, wherein said diameter is substantially 15 mm.

14. A medical device according to claim 1, wherein said housing and said mouthpiece are threaded together to attain predetermined rotational positions for controlling an amount of air flow through said second main air channels, said branch air channels, and said connecting channels.

15. A medical device according to claim 1, wherein said first main air channels extend over an entire length of said housing.

* * * * *